United States Patent [19]

Yabe et al.

[11] Patent Number: 4,745,470
[45] Date of Patent: May 17, 1988

[54] ENDOSCOPE USING A CHIP CARRIER TYPE SOLID STATE IMAGING DEVICE

[75] Inventors: Hisao Yabe; Teruo Eino, both of Hachioji, Japan

[73] Assignee: Olympus Optical Co., Ltd., Tokyo, Japan

[21] Appl. No.: 33,954

[22] Filed: Apr. 3, 1987

[30] Foreign Application Priority Data

Apr. 4, 1986 [JP] Japan .................................. 61-77825

[51] Int. Cl.⁴ ............................................. H04N 7/18
[52] U.S. Cl. ......................................... 358/98; 128/6
[58] Field of Search ...................... 358/98, 229; 128/4, 128/6

[56] References Cited

U.S. PATENT DOCUMENTS

| | | | |
|---|---|---|---|
| 4,491,865 | 1/1985 | Danna et al. | 358/98 |
| 4,519,391 | 5/1985 | Murakoshi | 128/303.15 |
| 4,539,586 | 9/1985 | Danna et al. | 358/98 |
| 4,573,450 | 3/1986 | Arakawa | 128/6 |

FOREIGN PATENT DOCUMENTS

| | | | |
|---|---|---|---|
| 3542761 | 6/1986 | Fed. Rep. of Germany | 358/98 |
| 60-24101 | 5/1984 | Japan . | |
| 0066224 | 4/1985 | Japan | 358/98 |

Primary Examiner—Howard W. Britton
Assistant Examiner—Victor R. Kostak
Attorney, Agent, or Firm—Armstrong, Nikaido, Marmelstein & Kubovcik

[57] ABSTRACT

A solid state imaging device and a substrate to which this solid state imaging device is fitted is contained in the tip part of an endoscope. Conductive parts are formed on at least one side surface of the substrate. The positions of the conductive parts, when that the conductive parts are overlapped with the solid state imaging device, are retreated to be within the electrode positions of the solid state imaging device so that the imaging device may be contained in a small space.

22 Claims, 18 Drawing Sheets

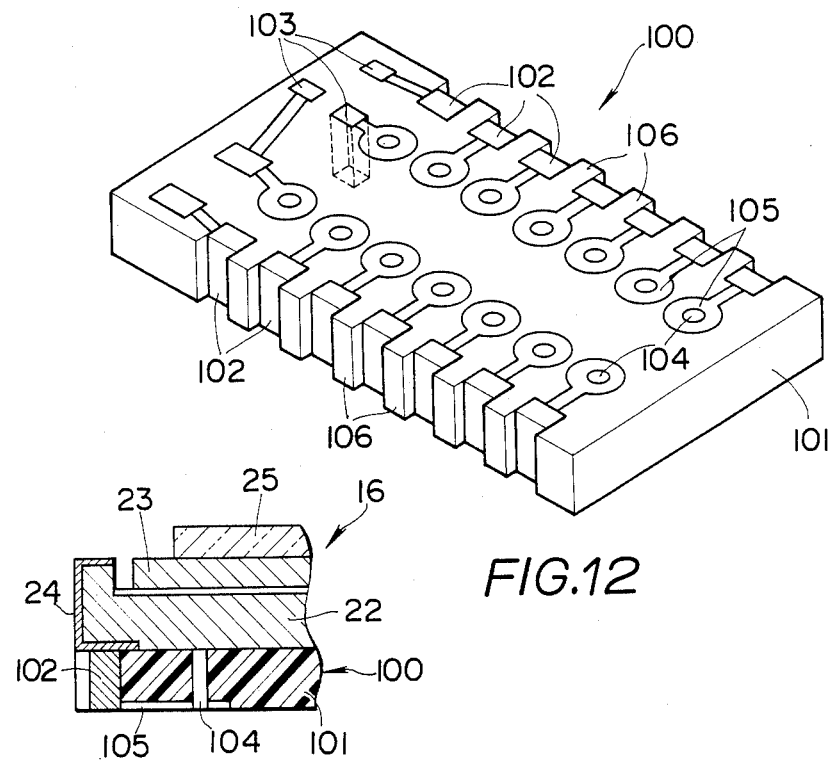
FIG.12
FIG.13
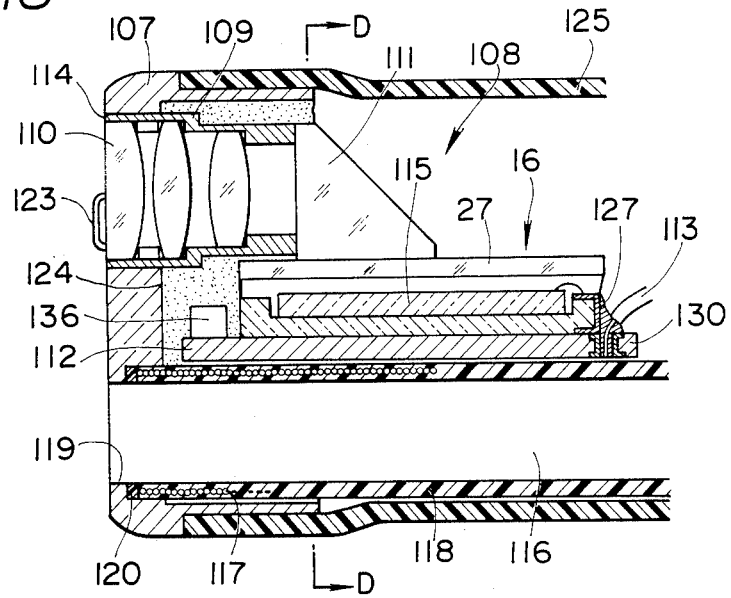
FIG.14

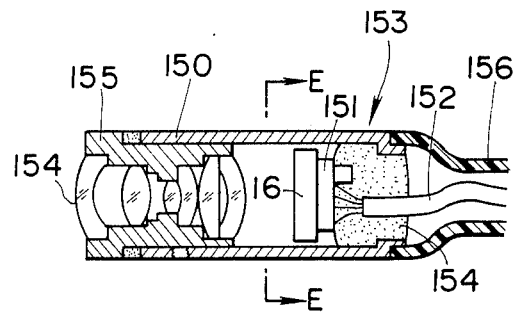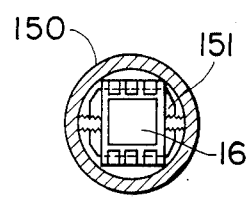
FIG.18  FIG.19
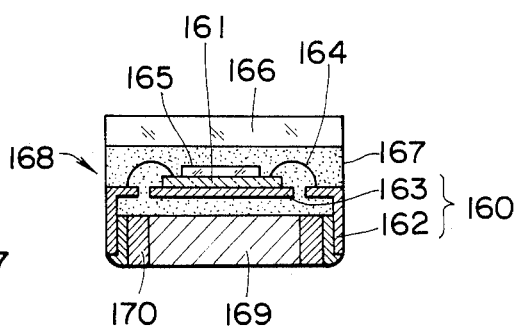
FIG.20  FIG.21

4,745,470

ENDOSCOPE USING A CHIP CARRIER TYPE SOLID STATE IMAGING DEVICE

BACKGROUND OF THE INVENTION

Field of the Invention and Related Art Statement

This invention relates to an endoscope provided at the tip with a solid state imaging device.

There has been already suggested an endoscope provided in the tip part with a solid state imaging device. In such endoscope, in the tip part, not only a solid state imaging device but also electronic parts forming amplifiers and others are incorporated and further many cables are connected.

As shown, for example, in FIG. 2 of the publication of Japanese Patent Laid Open No. 241010/1985, a solid state imaging device arranged axially in the tip part of an endoscope is attached to a substrate of a width in the diametral direction larger than that of the solid state imaging device and has electronic parts and cables connected to the surface opposite the surface to which the solid state imaging device is attached to the substrate.

In the prior art, as the width of the substrate was larger than the width of the solid state imaging device, the diameter of the endoscope tip part was large. Therefore, the endoscope was likely to give the patient a pain larger than was necessary when it was inserted.

Also, in U.S. Pat. No. 4,491,865, as the width of the substrate is larger than the width of the solid state imaging device, there is the same defect.

Also, in U.S. Pat. No. 4,519,391, as the solid state imaging device and imaging circuit are covered with an enclosure, there is a defect that the outside diameter of the tip part is large.

On the other hand, in U.S. Pat. No. 4,573,450, amplifiers and others are not incorporated and the substrate part is not clearly shown but a solid state imaging device showing a width considerably larger than the image area is used (the substrate and solid state imaging device may be shown as combined however) and therefore it is difficult to make the contour of the tip part small.

OBJECTS AND SUMMARY OF THE INVENTION

An object of the present invention is to provide an endoscope wherein the outside diameter of the tip part can be made smaller.

Another object of the present invention is to provide an endoscope which can be used for wide uses.

According to the present invention, in an endoscope containing in the tip part a solid state imaging device and a substrate to which this solid state imaging device is attached, conductive parts are formed on the side surfaces of the substrate. At least a part of the electrodes of the solid state imaging device are flushed with or projected from these conductive parts and the electrodes and conductive parts are electrically connected with each other while the solid state imaging device and substrate are directly laminated so that the tip part may be made smaller in the diameter.

BRIEF DESCRIPTION OF THE DRAWINGS

FIG. 1 is a sectioned view of an endoscope tip of the first embodiment.

FIG. 2 is a sectioned view on line A—A in FIG. 1.

FIG. 3 is a sectioned view in the short axis direction of the imaging part of the same embodiment.

FIG. 4 is a sectioned view on line B—B in FIG. 3.

FIG. 5 is a view as seen from above of a solid state imaging device of the same embodiment.

FIG. 6 is a sectioned view on line C—C in FIG. 5.

FIG. 7 is a perspective view of a substrate of the same embodiment.

FIG. 8 is a schematic view of the solid state imaging device of the same embodiment.

FIG. 9 is an electric wiring diagram of the same embodiment.

FIG. 12 is a perspective view of a substrate of the third embodiment.

FIG. 13 is a partial sectioned view of the substrate and solid state eimaging device as laminated of the same embodiment.

FIG. 14 is a sectioned view in the axial direction of an endoscope tip part of the fourth embodiment.

FIG. 18 is a sectioned view in the axial direction of the fifth embodiment.

FIG. 19 is a sectioned view on line E—E in FIG. 18.

FIG. 20 is a partial sectioned view of a substrate and solid state imaging device of the sixth embodiment.

FIG. 21 is a sectioned view of the seventh embodiment.

FIGS. 31 to 36 relate to the sixteenth embodiment of the present invention.

FIG. 31 is a sectioned view of a tip part of the sixteenth embodiment.

FIG. 32 is an elevation of the tip part.

FIG. 33 is a sectioned view on line F—F in FIG. 31.

FIG. 34 is a magnified view of the solid state imaging device and substrate part in FIG. 33.

FIG. 35 is a magnified view of the solid state imaging device and substrate part in FIG. 31.

DETAILED DESCRIPTION OF PREFERRED EMBODIMENTS

Figure 1:
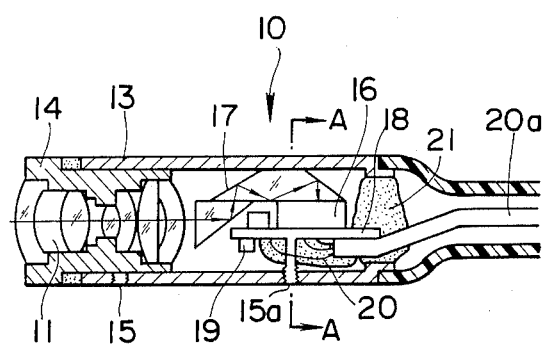
FIGS. 1 to 9 relate to the first embodiment of the present invention.
Figure 2:
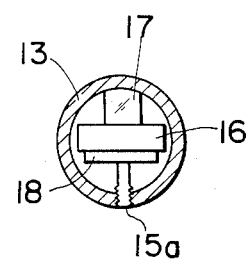

As shown in FIGS. 1 and 2, an endoscope by the first embodiment of this invention has an objective optical system 11 and imaging part 12 within a tip forming part of the endoscope. The objective optical system 11 is fitted in a lens frame 14 fitted to the tip part of a cylindrical frame body 13 of the tip forming part 10. This objective optical system 11 is adjusted in focusing by sliding the frame body 13 in the axial direction and is provisionally fixed with a screw 15 and then the lens frame 14 and frame body 13 are fixed with cement.

The imaging part 12 comprises a solid state imaging device 16 provided in parallel with the long axis of the tip forming part 10, a prism 17 fitted to a light receiving surface of this solid state imaging device and a substrate 18 fixed to the back surface of the solid state imaging device 16. The prism 17, is to lead an optical image from the objective optical system 11 to the light receiving part of the solid state imaging device 16. As shown in FIG. 2, the top part not used for the reflecting surface of the prism 17 is formed to be of a shape along the inner peripheral surface of the frame body 13.

To the substrate 18 are attached an electronic part 19 and coaxial cables 20 transmitting and receiving signals between the solid state imaging device 16 and an external device. These cables 20 are bundled within the tip forming part 10 and are inserted through the insertion part of the endoscope. The imaging part 12 is fixed to the frame body 12 with a screw 15a and is sealed and fixed with a cement 21 in the base end part of the frame body 13.

Figure 3:
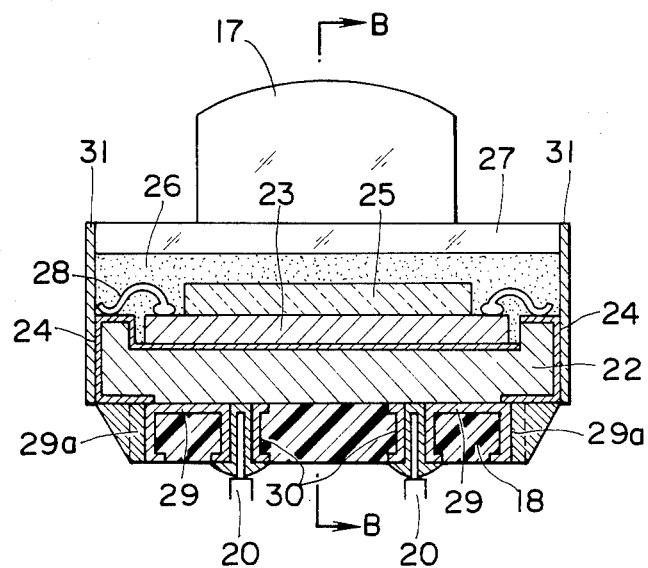

FIG. 3 is a sectioned view in the short axis direction of the imaging part 12.

In the solid state imaging device 16, a semiconductor image sensor chip 23 is die-bonded to a ceramic base 22 and the substrate 18 is soldered on the other side of the ceramic base 22. The ceramic base 22 is of a so-called chip carrier type having electrodes formed on the outside surfaces. Electrodes 24 are connected to the chip 23 through bonding wires 28. A color filter array 25 is pasted to the chip 23 with an ultraviolet ray setting cement or the like. Further, the light receiving part of the chip 23 is sealed with a light transmitting resin 26 such as an acrylic resin and has a cover glass 27 pasted on the surface. In such case, the color filter array 25 may be of a gelatin filter. The light transmitting resin may be replaced with a low melting point glass. In such a case, a heatproof glass is used for the cover glass and a dichroic filter is used for the color filter array. Further, an infrared ray absorbing filter may be used for the cover glass 27. Also, an infrared ray interfering filter coating or visible light reflection preventing coating may be applied to the cover glass 27. In such a case, if the coating is applied to the inside, the cementing force of the light transmitting resin 26 will be reduced. Therefore, it is preferable to apply the coating to the outside of the cover glass 27. A prism 17 is cemented to the outer surface of the cover glass 27.

One of the electrodes 24, provided on the ceramic base 22, is connected with the back surface of the chip 23 to give a reference potential. The other electrodes 24 are connected respectively with the chip 23 only through the bonding wires 28 to receive and transmit various signals. Also, the electrodes 24 extend to the back surface of the ceramic base 22. Here, conductive parts 29 of the substrate 18 and the electrodes 24 are soldered to be fixed with each other. This soldering may be replaced with a conductive cement.

The substrate 18 is provided with through holes 30 through which the respective cables 20 are inserted in the end parts and are soldered. As shown in FIG. 3, the width of the cross-section in the diametral direction of the endoscope of the substrate 18 is made smaller than the width of the solid state imaging device 12.

After the electrodes 24 are connected with the substrate 18, the solid state imaging device 12 is coated on the peripheral side surfaces with a film 31 which is low in ventilation such as polyvinylidene chloride, vinylon, K-coated cellophane, polypropylene, polyester or nylon.

Figure 4:
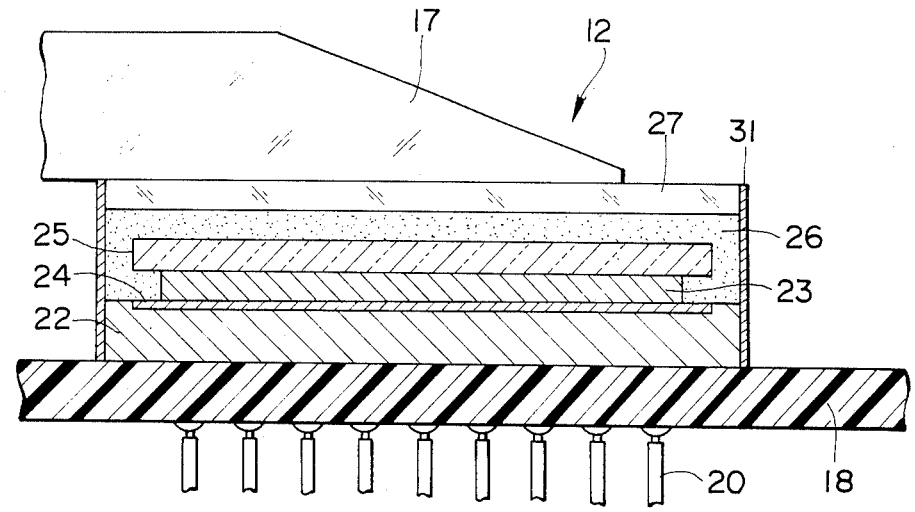
Figure 5:
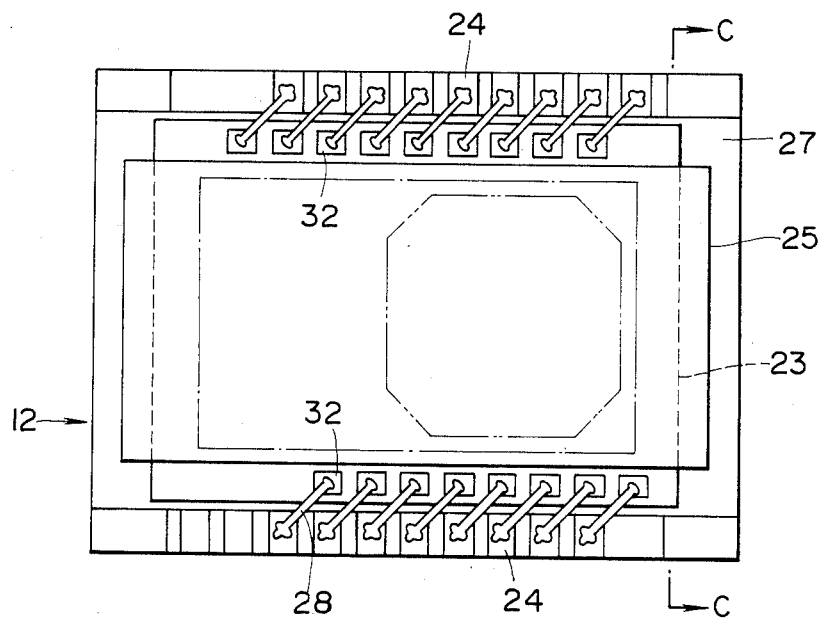
Figure 6:
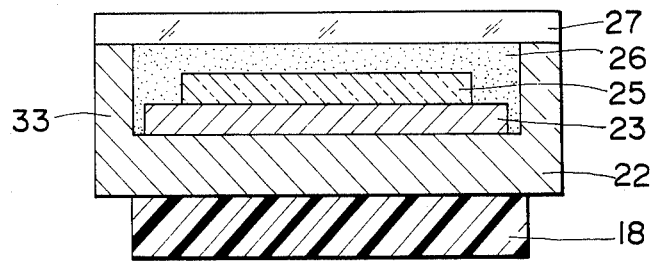

As shown in FIGS. 4, 5 and 6, the color filter array 25 is formed to be longer than the chip 23 in the long axis direction of the solid state imaging device and to be shorter than the chip 23 in the short axis direction. Further, as shown in FIG. 5, the bonding wire 28 is diagonally hung between the electrode 24 of a ceramic package 22 and the chip 23. The light receiving part of the chip 23 is the range indicated by the one-point chain line in FIG. 5 but only a part of it as indicated by the two-point chain line in FIG. 5 may be used. Further, the ceramic base 22 is provided in the four corners with projections 33 in contact with the cover glass 27 as shown in FIG. 6 so that the parallelism of the cover glass 27 with the chip 23 plane may be high.

Figure 7:
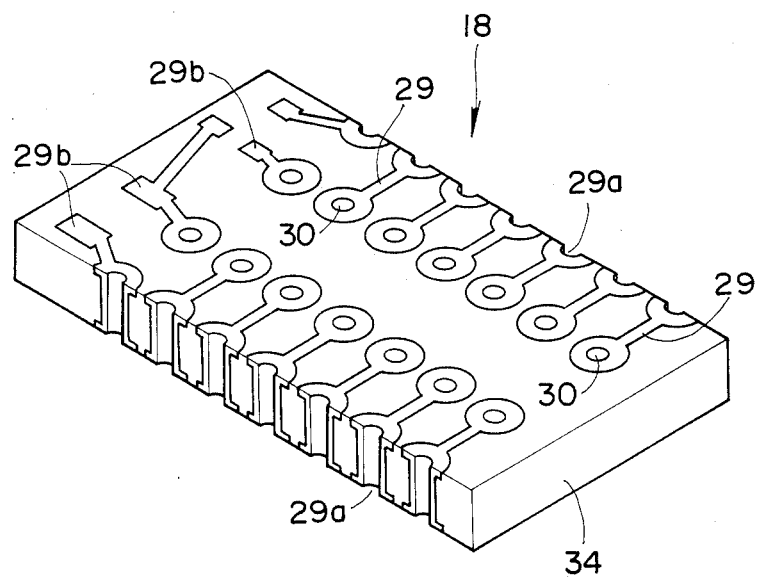

As shown in FIG. 7, the substrate 18 has the conductive parts 29 formed on an insulating part 34 made of a synthetic resin and is provided with through holes 30 for conductors at predetermined intervals. The conductive parts 29a on the side surfaces of this substrate are connected by soldering respectively with the electrodes 24 of the solid state imaging device 12. Each conductive part 29a is formed by providing the substrate 18 with a through hole and cutting off the end part of the substrate 18 so that more than half of the through hole may remain. The conductive parts 29b to which such parts as transistors and capacitors are attached are formed on the surface of the substrate 18.

The solid state imaging device used in this embodiment shall be explained in the following.

Figure 8:
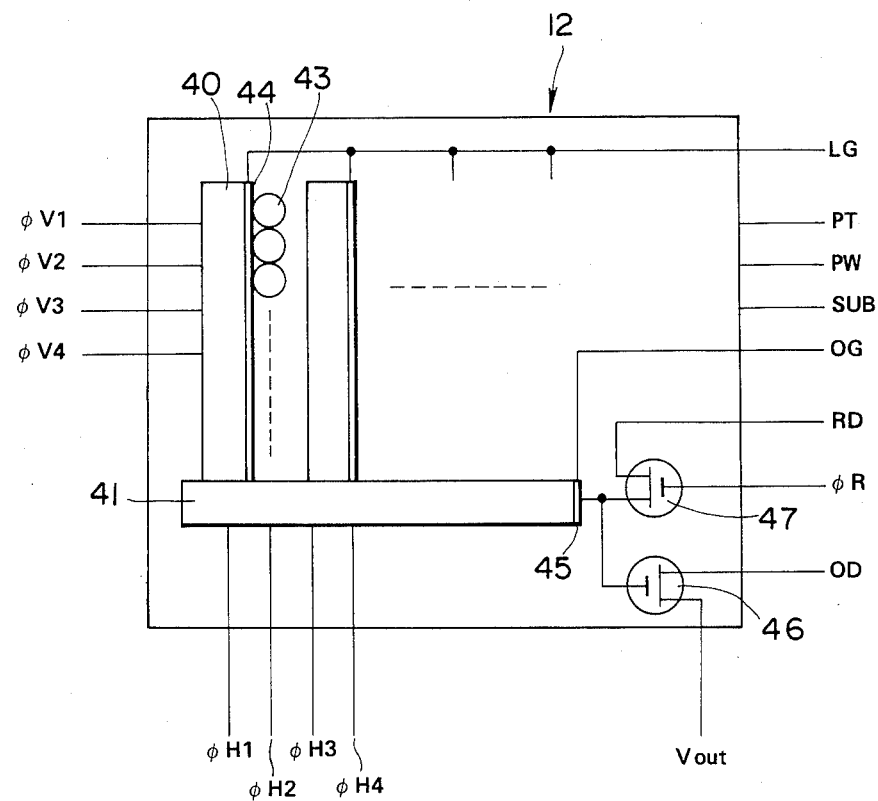

As shown in FIG. 8, a so-called CCD (charge coupled device) is used in this solid state imaging device 12. A vertical transferring CCD 40 and horizontal transferring CCD 41 are formed on the surface of the light receiving part of the imaging device 12 so that electric charges produced in the photodiode 43 may be transferred in turn. A load gate 44 is formed between the vertical transferring CCD 40 and photodiodes 43 so as to apply a direct current voltage of $+3V$ through a load gate terminal LG. The vertical transferring CCD 40 is driven when four-phase clock signals of $\phi V_1$, $\phi V_2$, $\phi V_3$ and $\phi V_4$ are applied and electric charges produced in the photodiodes 43 are read out and transferred at a predetermined timing. The horizontal transferring CCD 41 transmits line by line the charges transmitted from the vertical transferring CCD 40. The horizontal transferring CCD 41 is driven by the four-phase clock signals of $\phi H_1$, $\phi H_2$, $\phi H_3$ and $\phi H_4$. An output gate 45 is formed at the output end of the horizontal transferring CCD 41 and a direct current voltage of $+7V$ is applied. The signal charges output from this horizontal transferring CCD 41 are applied to the gate of an output FET (field effect transistor) 46 and signal outputs corresponding to the signal charges from the respective photodiodes are output from the source of the FET 46. A drain voltage is applied to the drain of the FET 46 from an output drain terminal OD. The gate of the FET 46 is connected also to the source of a resetting FET 47. After the signal outputs of the respective photodiodes are obtained, the electric charges applied to the gate of the FET 46 are made to escape from the resetting drain terminal RD through the drain of the FET 47 at a predetermined timing. A voltage of +16V is applied to the drain of each of these FET's 46 and 47. Also, a voltage of −7V is applied to a protective well terminal PT of the solid state imaging device 12, a voltage of OV is applied to a P well terminal PW and a voltage of +8V is applied to the substrate bias terminal SUB to give a predetermined reference potential.

Figure 9:
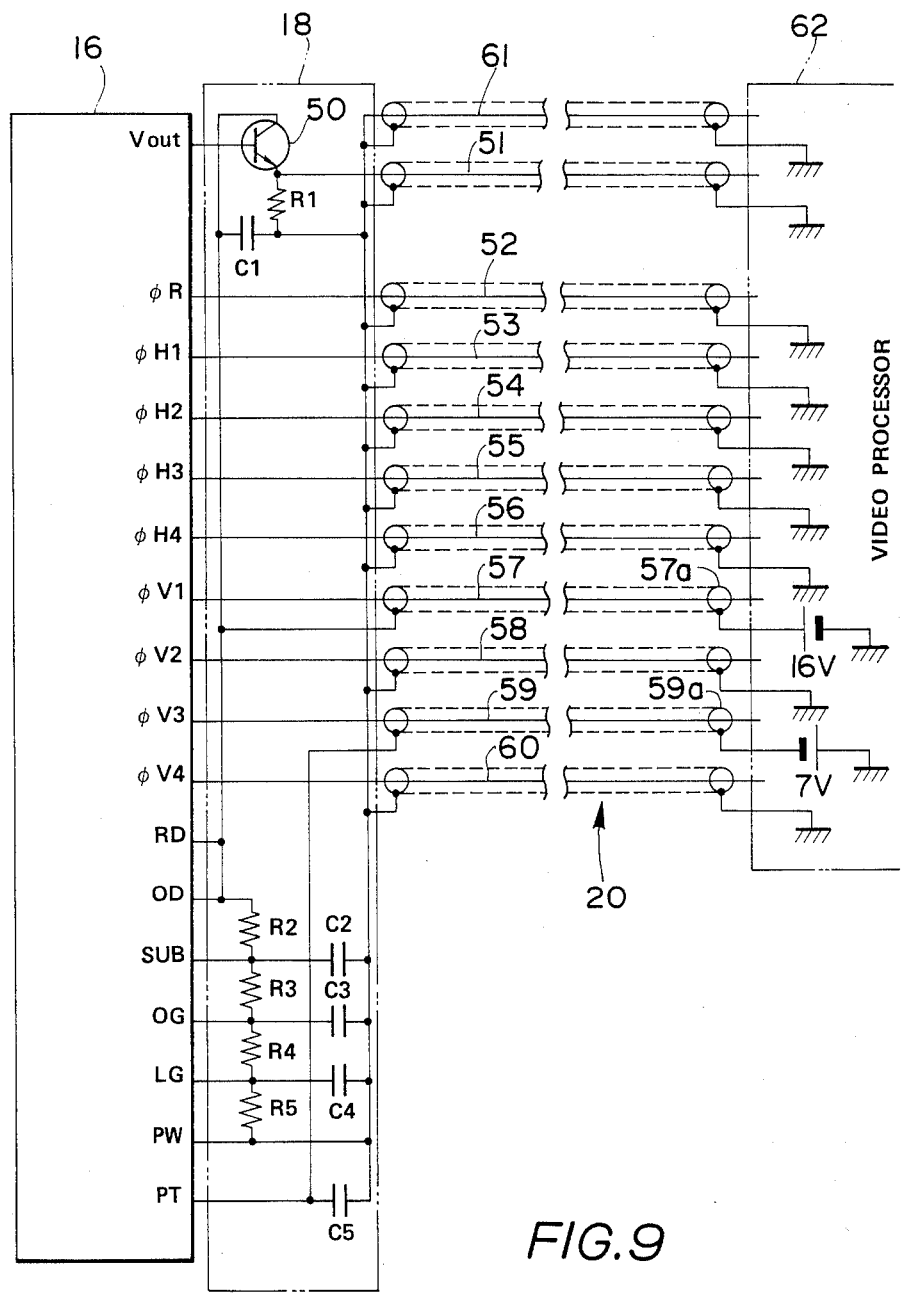

In the electric connection of this embodiment, as shown in FIG. 9, a signal output terminal $V_{out}$ of the solid state imaging device 16 is connected to an output buffer transistor 50 and the output signal is amplified and is led to a circuit (not illustrated) within a video processor 62 through a coaxial cable 51. This output buffer transistor 50 is provided on the substrate 18 together with another resistance $R_1$ and capacitor $C_1$. A cable 52 is connected to a resetting terminal R, cables 53, 54, 55 and 56 are connected respectively to horizontal driving pulse $\phi H_1$, $\phi H_2$, $\phi H_3$ and $\phi H_4$ terminals and cables 57, 58, 59 and 60 are connected respectively to vertical driving pulse $\phi V_1$, $\phi V_2$, $\phi V_3$ and $\phi V_4$ terminals. Further, the picture signal cable 51 is provided as paired with a dummy cable 61 for canceling noises. A shielding wire 57a for the cable 57 is utilized as a line for transmitting direct current signals of +16V. A shielding wire 59a for the cable 59 is utilized as a line for transmitting direct current signals of −7V. Shielding wires for the other cables are grounded at OV.

A direct current voltage of +16V is applied to the terminals RD and OR of the solid state imaging device 12 through the shielding wire of the cable 57. The above mentioned voltage of +16V is divided and is applied to the terminals RD and OD of the solid state imaging device 12 through the shielding wire of the cable 57. The above mentioned voltage of +16V is divided and is applied to the terminals SUB, OG, LG and PW repsectively through resistances $R_2$, $R_3$, $R_4$ and $R_5$. A direct current voltage of −7V is applied to the terminal PT through the shielding wire of the cable 59. Capacitors $C_1$, $C_2$, $C_3$, $C_4$ and $C_5$ are connected to the terminals RD, OD, SUB, OG, LG and PT on which the direct current voltage is applied and are grounded as of an alternating current.

The cables 51, 52, 53, 54, 55, 56, 57, 58, 59, 60 and 61 are connected to the video processor 62 by a connector (not illustrated) through the insertion part, operating part and universal cord of the endoscope.

In the endoscope by this embodiment, an observed image is formed on the light receiving surface of the image sensor chip 25 of the solid state imaging device 16 through the objective optical system 11 and prism 17. This observed image is converted to an electric signal of a time series by the solid state imaging device 16 and the electric signal is put into the video processor 62 by the coaxial cable 20. Within this video processor 62, the electric signal is treated as predetermined by a treating circuit not illustrated so that the observed image may be observed by a TV monitor.

The effects of this embodiment shall be explained in the following.

According to this embodiment, within the frame body 13, the imaging part 12 such as the prism 17 is fixed and the lens frame 14 is slid so as to set focusing. Therefore, the optical system can be made as a unit to increase the strength of the device.

Also, as the width of the substrate 18 is made smaller than the width of the solid state imaging element 16, the space within the endoscope tip forming part 10 can be effectively utilized to arrange component parts and to make the endoscope smaller in diameter. Further, as the electronic part 19 on the substrate 18 is arranged between the prism 17 and solid state imaging device 16, the tip forming part can be made smaller.

Also, as the solid state imaging device 16 is of a so-called chip carrier type, the package is smaller and thus contributes to making the tip forming part smaller.

Further, the tip forming part (tip part) can be made smaller in the diameter, therefore can be used through an inserting course of a smaller diameter and can be used for extensive purposes. Also, as the tip part can be made smaller in the diameter, the pain given to the patient in inserting it can be reduced.

Further, as the solid state imaging device 16 is coated on the sides with the film 31 having no ventilation. Thus, even if the endoscope is sterilized with ethylene oxide gas, the light transmitting resin 26 and chip 23 will not be affected by this gas.

On the surface of the solid state imaging device 16 side of the substrate 18, a resist is provided on the electrodes and lands, so that no solder bridge will be produced between the lands and between the electrodes.

Within the solid state imaging device 16, the length in the long axis direction of the color filter array 25 is longer than the chip 23. No projection of the ceramic base 22 is provided on the end surface in the long axis direction and therefore it is easy to position the color filter array. Further, the wire bonding of the chip 23 and ceramic base 22 is formed without opposing the bonding pads on the side surfaces with each other. Therefore, the distance between the chip and the base can be made longer without making the clearance large and the bonding work is easy.

In this embodiment, the color filter array 25 is provided in the solid state imaging device 16 but will not be required in the case of a color imaging system in the order of planes by an illuminating light.

The second embodiment of the present invention shall be explained in the following on the basis of FIGS. 10 and 11. Here, the same members as in the above mentioned first embodiment shall respectively bear the same reference numerals and shall not be explained.

Figure 11:
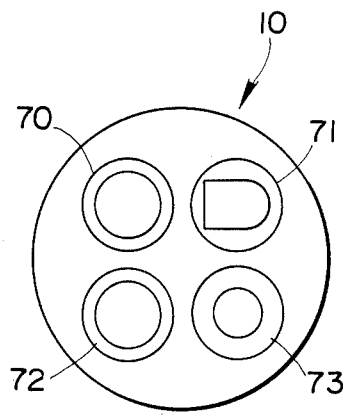
FIG. 11 is an elevation of the tip of the same embodiment.

In the endoscope of this embodiment, as shown in FIG. 11, an imaging unit 70, air and water feeding unit 71, illuminating unit 72 and forceps channel unit 73 are respectively embedded within the chip forming part 10.

Figure 10:
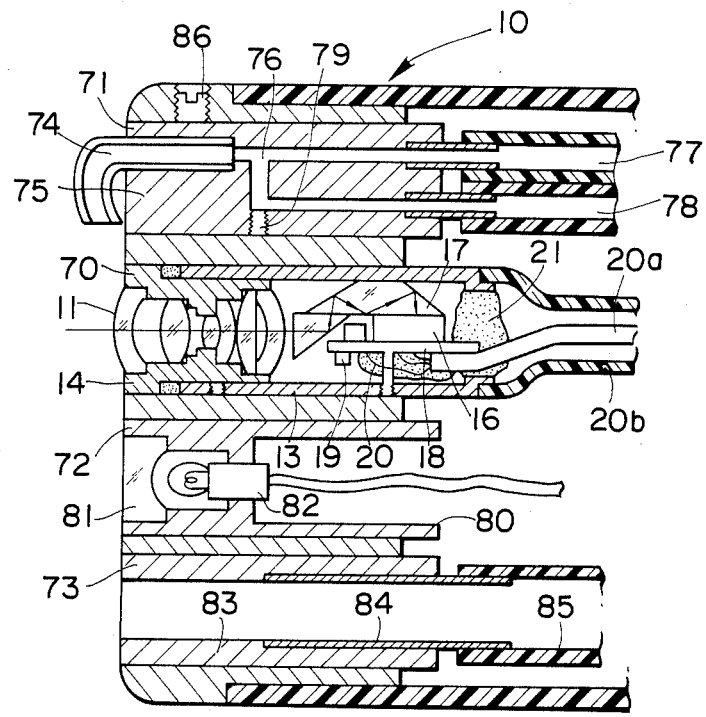
FIG. 10 is a sectioned view of a tip of the second embodiment.

FIG. 10 is a sectioned view provided with the sections of the respective units.

The air and water feeding unit 71 is formed of a nozzle 74 fitted to a nozzle body 75 with which an air and water feeding path 76 joins in the course. The air and water feeding path 76 is connected respectively to an air feeding channel 77 and water feeding channel 78. A screw 79 is to clog a hole in use.

The imaging unit 70 is fitted with a unit of the same formation as of the endoscope of the first embodiment. Here, the coaxial cables 20 are bundled within a flexible tube 20a and are inserted through the insertion part. Further, this flexible tube 20a is protected by a protective tube 20b fixed to the frame body 13.

The illuminating unit 72 has a lens 81 fitted in a cylindrical supporter 80 and a lamp 82 fitted in the rear of the lens 81.

The forceps channel unit 73 is formed of a connecting tube body 84 fitted to a cylindrical mouthpiece 83 and a channel tube 85 connected to the connecting tube body 84.

The respective units are fixed by a screw 86 and are sealed with a cement or the like.

The up direction of the endoscope of this embodiment is equal to the up direction in FIG. 11.

As compared with the endoscope of the first embodiment, the endoscope of this embodiment has an air and water feeding function, illuminating function and forceps channel and therefore various medical treatments are possible with it.

Further, the endoscope is formed by combining the respective functions in the respective units and is very high in the assemblability and repairability.

FIGS. 12 and 13 show the third embodiment of the present invention. FIG. 12 shows another embodiment of the substrate 18 of the first embodiment shown in FIG. 7. This substrate 100 is formed by inserting electrodes 102 of conductive parts in an insulating part 101 such as plastic and conductive members in lands 103 for connecting electric elements. Through holes 104 for connecting cables are formed on the insulating part 101 and lands 105 are printed with a conductive paint only on the surfaces. Circuits are printed with the conductive paint between the electrodes 102 and the respective lands 103 and 105. Each electrode 102 is fitted in a recess made on the side surface of the substrate 100 to have a step. FIG. 13 is a partial sectioned view of the substrate 100 and solid state imaging device of the third embodiment arranged as laminated. The side surface on the electrode 102 side of the substrate 100 is substantially flush with the side surface of the substrate 100 or is arranged somewhat inside and the electrodes 102 of the substrate 100 and the electrodes 24 of the solid state imaging device 16 are contacted and connected by soldering with each other. The cable is inserted through the through hole 104 and is connected with the land 105 by soldering.

According to the substrate 100 of the third embodiment, as there is a projecting wall 106 between the respective electrodes, no bridge will be produced between the electrodes when connected with the electrodes 24 of the solid state imaging device 16.

In this embodiment, the side surface position of the solid state imaging device 16 and the side surface position of the substrate 100 coincide with each other.

Figure 15:
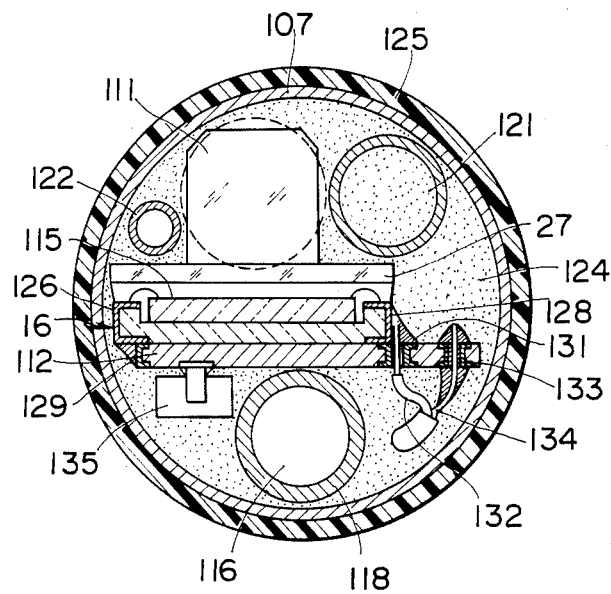
FIG. 15 is a sectioned view on line D—D in FIG. 14.
Figure 16:
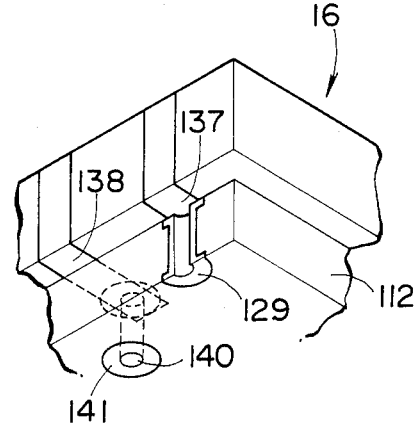
FIG. 16 is a partial sectioned view of the same embodiment.

The fourth embodiment of the present invention is shown in FIGS. 14 to 17. FIG. 14 is a sectioned view in the axial direction of the tip part of the endoscope. FIG. 15 is a sectioned view on line D—D in FIG. 14. FIG. 16 is a partial perspective view showing the position relation of the electrodes of the solid state imaging device 16 and substrate. Each of FIGS. 17A and 17B is a partial sectioned view showing the connection of the cable to the substrate electrode. In this fourth embodiment, respective members are made units and are inserted and fixed in a tip metal member 107. First of all, in an imaging system 108, a lens 110 is inserted and fixed in a lens frame 109 and a prism 111 converting the optical axis at right angles is cemented and fixed on the incident surface to the rear end of the lens frame 109. The prism 111 is opposed on the emitting surface to the imaging surface of the solid state imaging device 16 and is cemented and fixed on the cover glass 27. The solid state imaging device 16 is further fitted on the lower surface with a substrate 112 and has a cable 113 connected to it. In the imaging system 108, as shown in FIGS. 14 and 15, the lens frame 109 is inserted and fixed in an opening 114 of the tip metal member 107. At this time, the imaging surface 115 of the solid state imaging device 16 is so arranged as to substantially include the center axis of the endoscope. A forceps channel system 116 consists of a plastic tube 118 having a metallic coil pipe 117 incorporated within and high in the slidability. An opening 119 is formed with a step inside so as to pass on the under side of the substrate 112 located somewhat below the middle of FIG. 15 of the tip metal member 107. In the opening 119, an annular insulating plate 120 is arranged and the channel system 116 is inserted and fixed. For the tube 118 of this channel system 116, a metal blade, metal foil or the like may be incorporated instead of the metallic coil pipe 117. Such various incorporating manners as integral molding and lamination can be considered. Such metal part is not exposed to the inside diameter and outside diameter parts of the channel system 116, is connected to the ground of the circuit within the operating part and is formed to be non-conductive to the tip metal member 107.

In the tip metal member 107, a light guide system 121 is inserted and fixed in its opening, an air and water feeding tube system 122 is inserted and fixed in its opening and a nozzle 123 is arranged at the tip as directed toward the lens surface of the imaging system 108.

Within the tip metal member 107, the above mentioned various members are inserted and the spaces among them are filled with a cement 124. A cylindrical jacket tube 125 is connected and fixed to the tip metal part 107.

The relation between the solid state imaging device 16 and the substrate 112 in this fourth embodiment shall be explained in the following. In the solid state imaging device 16, electrodes 126, 128 and 127 are formed on the three sides of both left and right sides as seen toward FIG. 15 and the rear end side. The substrate 112 is projected from the sides of the solid state imaging device 16 at the front and rear ends and at the right end and is positioned inside the side of the solid state imaging device only at the left end. The electrode 126 of the solid state imaging device and the electrode 129 of the substrate are connected with each other by soldering and connecting the electrode pattern of the solid state imaging device and the electrode of the substrate with each other at the left end. The electrodes 127 and 128 of the solid state imaging device provided at the rear end and right end are connected with the electrodes 130 and 131 provided together with through holes by soldering and by inserting cables 113 and 132 in the through holes. A shielding wire 134 is soldered from below the substrate to an electrode 133 provided on the substrate 112 provided to project from the right end in the diametral direction of the solid state imaging device 16. Further, lands connecting such electronic parts as, for example, transistors and circuit patterns are provided on the lower surface of the substrate to connect and fix an electronic part 135 by avoiding the channel system. Circuit patterns are formed from the substrate 112 provided to project from the front end of the solid state imaging device 16 to connect and fix such electronic parts as resistances. These electronic parts 135 and 136 and cable 132 are provided within the range filled with the cement.

Figure 17A:
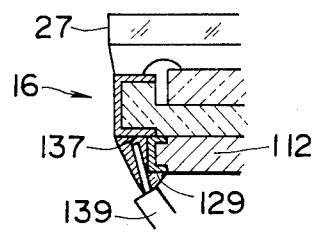
FIGS. 17A and 17B are partial sectioned views showing cables as connected.
Figure 17B:
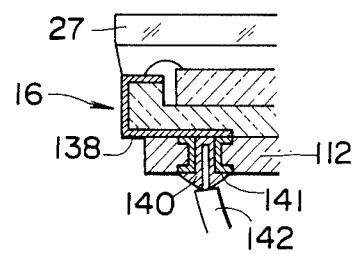

Further, as shown in FIG. 16, short electrode patterns 137 and long electrode patterns 138 are also formed on the back surface of the package of the solid state imaging device 16. The electrode pattern 137 is connected by soldering as paired with the electrode provided on the side surface of the substrate 112. In this case, as shown in FIG. 17A, a cable 139 is simultaneously soldered. For the electrode pattern 138, a through hole 140 and electrode 141 are provided on the corresponding substrate 112 and a cable 142 is inserted and soldered in the through hole 140 to be connected and fixed with both electrodes 138 and 141.

Now, FIGS. 18 and 19 show the fifth embodiment of the present invention. The fifth embodiment is a straight sight type endoscope wherein the imaging surface of a solid state imaging device is arranged vertically to the axis of the endoscope. FIG. 18 is a sectioned view in the axial direction. FIG. 19 is a sectioned view on line E—E in FIG. 18. In this fifth embodiment, an imaging system 153 of the solid state imaging device 16 and a substrate 151, as laminated and connected by soldering with a cable 152, is inserted into a frame body 150 from the front and is positioned and fixed with a screw or the like from the side. The frame body 150 is filled with a cement 154 from the rear end to fix the substrate 151, cable 152 and the like. A lens frame 155, internally fitted with an objective optical system 154, is inserted in the front of the frame body 150, is focused and is cemented and fixed. A jacket tube 156 of the endoscope insertion part is secured to the rear end of the frame body 150.

In this fifth embodiment, the width of the side on which electrodes are formed of the substrate 151 is made smaller than the width of the side on which electrodes are formed of the solid state imaging device 16. However, on the side on which no electrode is formed, the substrate 151 is formed to be wider than the solid state imaging device and is chamferred at the four corners to be modified.

The respective electrodes are connected with one another the same as in the above described respective embodiments.

FIG. 20 is a partial sectioned view showing the sixth embodiment of the present invention and shows only the side on which the respective electrodes 24 and 158 of the solid state imaging device 16 and substrate 157 are formed. In this sixth embodiment, the solid state imaging device 16 and substrate 157 are laminated by arranging the sides flush on which are formed the electrodes 24 and 158 and are soldered or cemented with a conductive cement on the sides.

FIG. 21 is a sectioned view showing the seventh embodiment of the present invention and shows the formation and external fitting manner of the solid state imaging device. In this seventh embodiment, electrodes are not formed on a base such as ceramics but a lead plate 161 is made of a metal plate and a solid state imaging device chip 161 is die-bonded on the lead plate 161. The lead plate 160 is formed by punching a metal plate to be of a shape in which an electrode 162 as connected on the periphery is left and downward bending the electrode 162 to be U-shaped. The thus formed lead plate 160 is held on a jig. The solid state imaging device chip 161 is laminated on the central part 163 of the lead plate 160 and is diebonded. The electrode of the chip 161 and the electrode 162 of the lead plate are connected with each other through bonding wires 164. Then, a color filter array 165 is positioned and laminated on the chip 161 and is secured with an ultraviolet ray setting cement. In this state, the cover glass 166 is held with a jig with a clearance above the color filter array 165 and the air gap including the central part 163 of the lead plate 160 and the electrode 162 and reaching the cover glass 166 is filled with a light transmitting resin 167 to integrally mold one solid state imaging device 168. Then, the peripheral part of the lead plate left, lest the electrode 162 of the lead plate 160 should be separated, is cut off to make the electrode 162.

The same as in the fitting structure made in the above described respective embodiments, in a solid state imaging device 168, a substrade 169 is laminated on the lower surface of the resin molded below the lead plate 160. The electrode of the solid state imaging device 168 is positioned as opposed to the electrode 170 provided on the side surface of the substrate. Both electrodes 162 and 172 are connected by soldering to each other.

Figure 22:
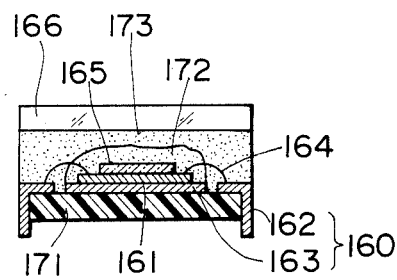
FIG. 22 is a sectioned view of the eighth embodiment.

FIG. 22 is a sectioned view showing the eighth embodiment of the present invention and shows only the structure of the solid state imaging device. In this eighth embodiment, the solid state imaging device chip 161 is die-bonded on the central part 163 of the lead plate 160 made the same as in the seventh embodiment and is bonded with bonding wires 164. The color filter array 165 is positioned and cemented on the chip 161. Then, the lead plate 160, fitted with the solid state imaging device chip 161, is mounted on a base 171 made of plastics or ceramics and the space is filled with the first transmitting resin 172 to cover the chip 161. Then, the cover glass 166 is positioned above with a jig or the like and the air gap from the cover glass 166 is filled with the second light transmitting resin 173. Here, resins having the same refractive index and the same thermal expansion coefficient are used for the first and second light transmitting resins 172 and 173. Light transmitting resins of exactly the same material may be also used. It is necessary to fill the space with such light transmitting resin usually in an environment comparatively high in cleanliness. However, the space may be filled with the first light transmitting resin 172 in an environment comparatively high in cleanliness but with the second light transmitting resin in an environment low in cleanliness. Therefore, in positioning the cover glass 166, the assembling works in an environment high in cleanliness can be reduced. The assembling machine restricting conditions can be reduced and the production cost can be made low. Also, the parallelism between the chip 161 and cover glass 166 is easy to precisely make which improves the yield. Within a clean room, no injection machine is required when the resin is filled and a dispenser will do. If the space from the cover glass 166 is filed with the second light transmitting resin 173, not only will the planeness be easier to make than when there is no cover glass 166 but also the first and second light transmitting resins 172 and 173 will not peel off each other even in an environment high in humidity or low in temperature.

The lead plate 160 may be fixed to the base 171 before the solid state imaging device chip 161 is die-bonded.

Figure 23:
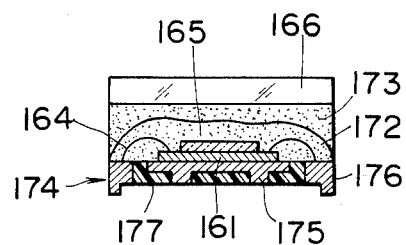
FIG. 23 is a sectioned view of the ninth embodiment.

FIG. 23 is a sectioned view showing the ninth embodiment of the present invention and shows only the structure of the solid state imaging device. In this ninth embodiment, in molding a base 174, a lead plate 175 and electrode 176 are embedded in plastics 177 by insertmolding. Then, the lead plate 175 surface on which the solid state imaging device chip 161 is to be die-bonded is ground and plated. The chip 161 is die-bonded on this surface. The electrode 176 and chip 161 inserted in the periphery of the base 174 are connected with each other through the bonding wires 164. Then, the same as in the eighth embodiment, the space is filled with the light transmitting resins 172 and 173.

In setting the light transmitting resins, the first light transmitting resin 172 is set at the normal temperature, is then taken out into an environment low in cleanliness and then may be heated to be set. Also, the first light transmitting resin 172 is set at the normal temperature and is then taken out into an environment low in the cleanliness and the second light transmitting resin 173 is injected and may be simultaneously heated to be set.

Figure 24:
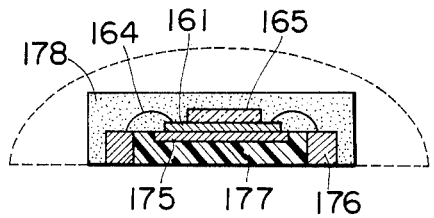
FIG. 24 is a sectioned view of the tenth embodiment.

FIG. 24 is a sectioned view showing the tenth embodiment of the present invention and shows only the structure of the solid state imaging device. In this tenth embodiment, the same as in the ninth embodiment, the electrode 176 and lead plate 175 are insert-molded in plastics, the solid state imaging device chip 161 is die-bonded, the electrode 176 and chip 161 are connected with each other through the bonding wires 164 and the color filter array 165 is positioned and cemented on the chip 161. Then, the light transmitting resin 178 is swollen as indicated by the broken line and is set so as to cover the entirety. This set resin 178 is ground on the periphery so as to be of any required size and is ground on the picture incident surface opposed to the chip 161 so as to be of a plane parallel with the chip 161.

The works up to swelling and forming the light transmitting resin 178 may be carried out within a clean room and the grinding on the periphery and upper surface may be carried out outside the clean room.

Figure 25:
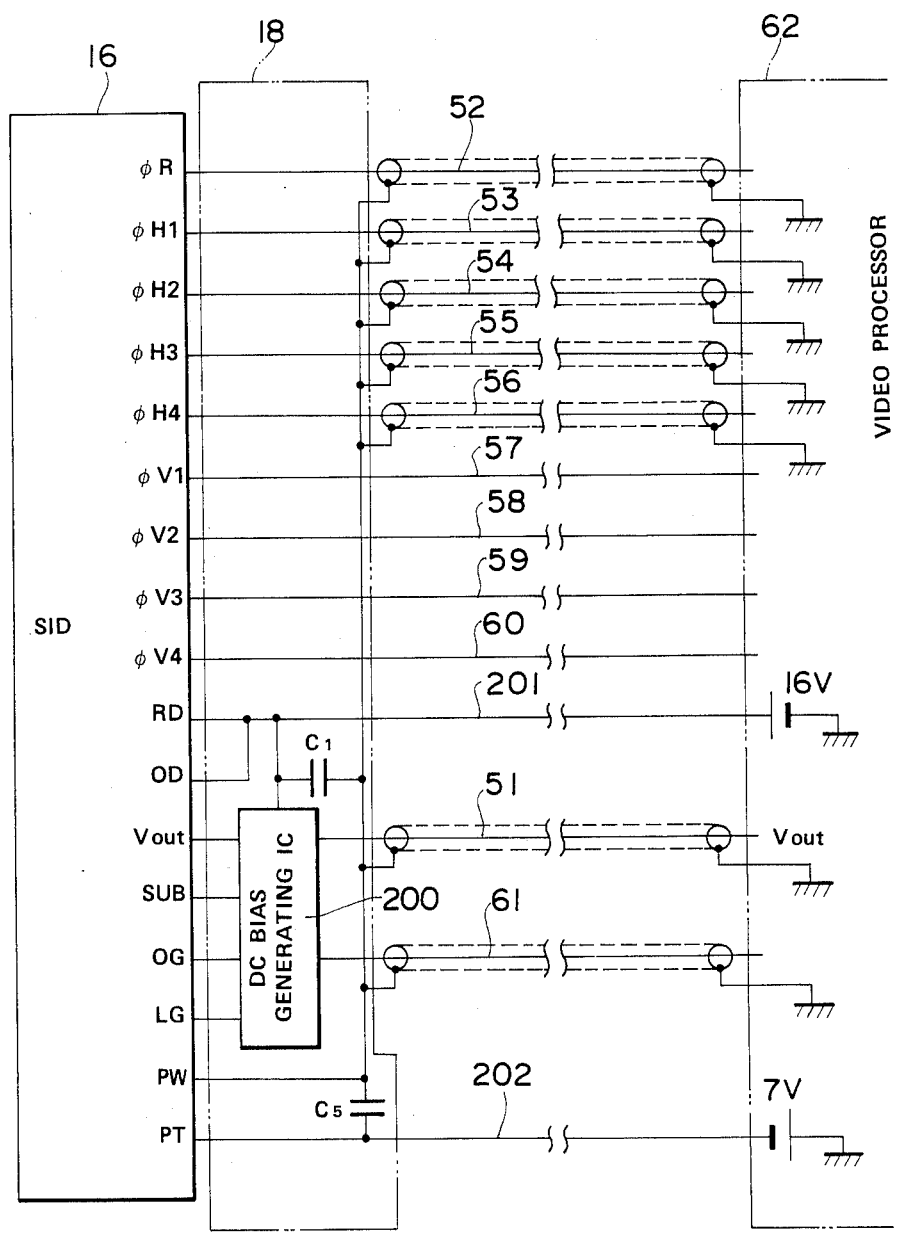
FIG. 25 is an electric circuit diagram of the eleventh embodiment.

The eleventh embodiment of the present invention shall be explained in the following on the basis of FIG. 25. Here, the same members as in the first embodiment shall bear respectively the same reference numerals and shall not be explained.

The same as in the first embodiment, resetting pulses and horizontally driving pulses to be input to the solid state imaging device 16 are fed from the video processor 62 through the coaxial cables 52, 53, 54, 55 and 56. Vertically driving pulses are fed from the video processor 62 through the non-shielded cables 57, 58, 59 and 60.

In this embodiment, the solid state imaging device 16 output terminal $V_{out}$, substrate bias terminal SUB, output gate terminal OG and load gate terminal LG are connected to the direct current bias generating IC 200. A direct current voltage of $+16V$ is input into the IC 200 from the video processor 62 and further a picture signal is amplified in this IC 200 and is output to the video processor 62 through the coaxial cable 51. A direct current voltage of $-7V$ is applied to the protective well terminal PT of the solid state imaging device 16 from the video processor 62 and the P well terminal PW is earthed to be of 0V. The cables 201 and 202 feeding direct current voltages of $+16V$ and $-7V$ are not shielded. Further, a direct current voltage of $+16V$ is applied to the resetting drain terminal RD and output drain terminal OD through the cable 201.

In this embodiment, a plurality of parts such as transistors fitted to the substrate 18 provided with the solid state imaging device 16 are replaced with one IC 200 and therefore the imaging part can be made small.

Also, the vertically driving pulses and direct current signals little influenced by high frequency noises are transmitted through the non-shielded cables 57, 58, 59, 60, 201 and 202, therefore the cable bundle can be made smaller in diameter and the endoscope can be made smaller in diameter.

Figure 26:
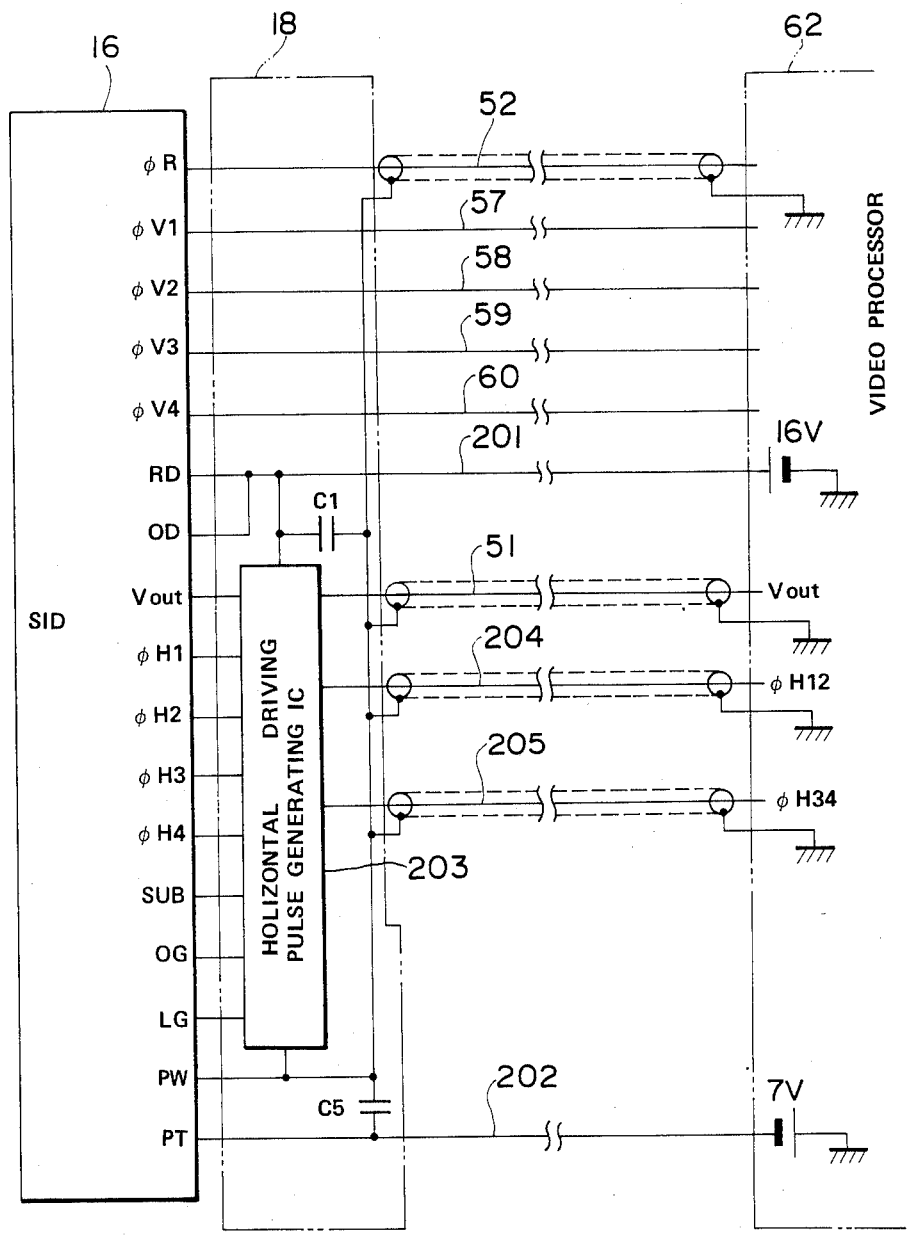
FIG. 26 is an electric circuit diagram of the twelfth embodiment.

The twelfth embodiment of the present invention shall be explained in the following on the basis of FIG. 26. Here, the same members as in the first embodiment shall bear respectively the same reference numerals and shall not be explained.

The resetting pulses to be input into the solid state imaging device 16 are fed from the video processor 62 through the coaxial cable 52. Also, the same as in the eleventh embodiment, the vertically driving pulses are fed through the cables 57, 58, 59 and 60. The non-shielded cables 201 and 202 are connected also to the output drain terminal OD, resetting drain terminal RD and protective well terminal PT. A direct current voltage of $+16V$ is fed respectively to the resetting drain terminal RD, output drain terminal OD and horizontally driving pulse generating IC 203 through the cable 201.

Figure 27:
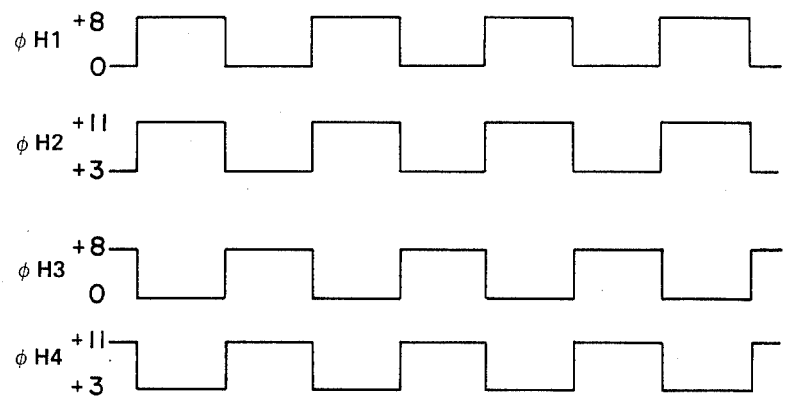
FIG. 27 is a clock pulse diagram of the same embodiment.

On the horizontally driving pulses, twophase clock signals $\phi H_{12}$ and $\phi H_{34}$ are fed to the IC 203 from the video processor 62 through the coaxial cables 204 and 205. As shown in FIG. 27, in the IC 203, these clock pulses are made two pairs of clock signals $\phi H_1$, $\phi H_2$ and $\phi H_3$, $\phi H_4$ which are the same in phase but are different in voltage level and which are fed respectively to the horizontally transferring clock terminals $\phi H_1$, $\phi H_2$, $\phi H_3$ and $\phi H_4$ of the solid state imaging device.

Thereby, two horizontally driving pulse signal transmitting cables can be reduced and the endoscope tip part can be made smaller in diameter.

Figure 28:
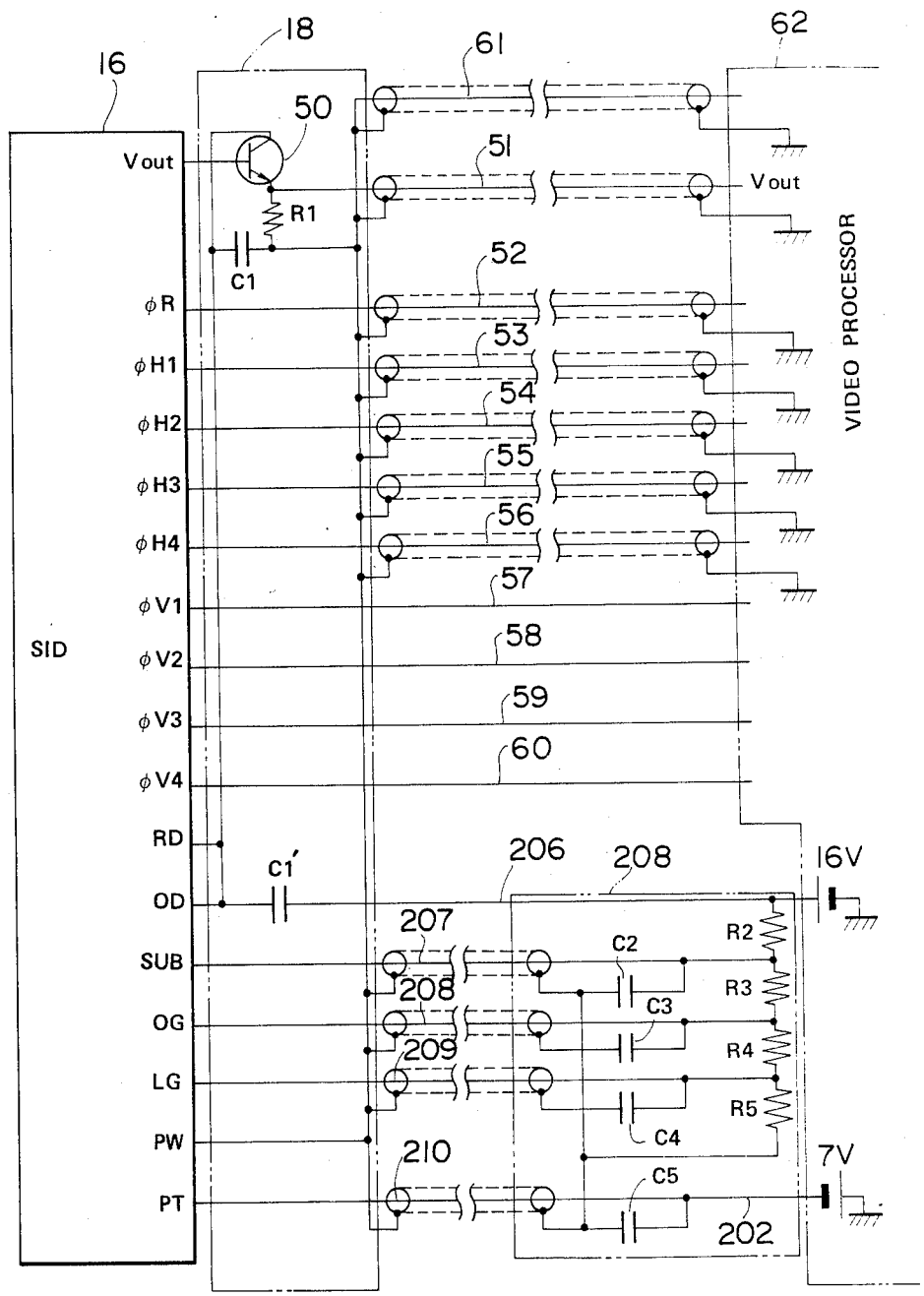
FIG. 28 is an electric circuit diagram of the thirteenth embodiment.

The thirteenth embodiment of the present invention shall be explained in the following on the basis of FIG. 28. Here, the same members as in the above described embodiments shall bear respectively the same reference numerals and shall not be explained.

In this embodiment, voltage dividing resistances $R_2$, $R_3$, $R_4$ and $R_5$ and capacitors $C_2$, $C_3$, $C_4$ and $C_5$ are not provided on the substrate 18 but are provided in the operating part. The other formations are substantially the same as in the first embodiment but the cables 57, 58, 59 and 60 for vertically driving pulses are shielded. The voltage dividing resistances $R_2$, $R_3$, $R_4$ and $R_5$ and capacitors $C_2$, $C_3$, $C_4$ and $C_5$ are provided within the endoscope operating part 208.

Within the operating part 208, a direct current voltage of $+16V$ is applied from the video processor 62 through the cable 206 and is divided by the voltage dividing resistances $R_2$, $R_3$ and $R_5$ and a predetermined voltage is applied to the respective terminals of the solid state imaging device through the coaxial cables 207, 208, 209 and 210. Here, the respective shielding wires are used as the extensions of the capacitors 207, 208, 209 and 210 and are variously matched as a whole.

Thereby, the electronic parts provided within the endoscope tip forming part can be minimized and the tip forming part can be made smaller in diameter.

Figure 29:
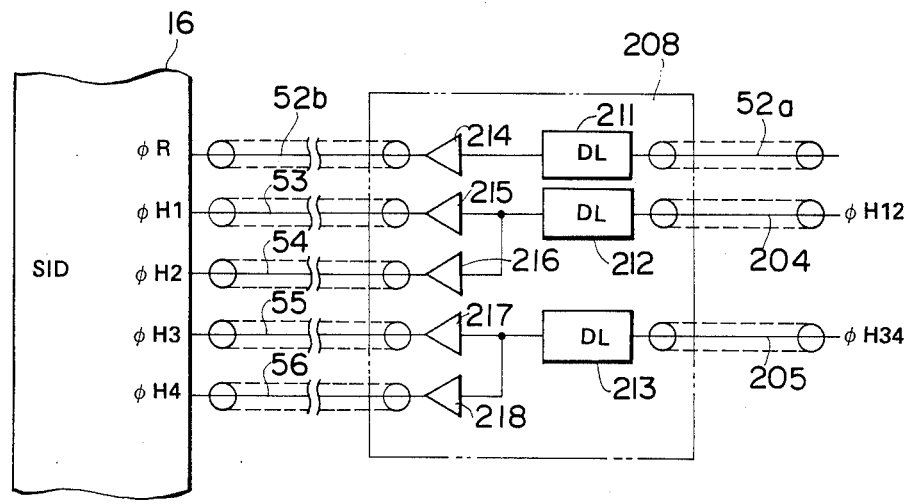
FIG. 29 is an electric circuit diagram of the fourteenth embodiment.

The fourteenth embodiment of the present invention shall be explained in the following on the basis of FIG. 29. Here, the same members as in the above described embodiments shall bear respectively the same reference numerals and shall not be explained.

In this embodiment, the same as in the thirteenth embodiment, the circuits for the solid state imaging device 16 are provided within the endoscope operating part but here the horizontally driving pulse phase compensating delaying circuits 211, 212 and 213 and drivers 214, 215, 216, 217 and 218 are provided. The drivers 214, 215, 216 217 and 218 are to regulate the waveforms of the driving pulses of the solid state imaging device 12 and to be driven with a predetermined voltage. The same as in the above described embodiment, the driving pulses are transmitted through the coaxial cables 53, 54, 55 and 56.

Also, the same as in the twelfth embodiment, two-phase clock pulses $\phi H_{12}$, and $\phi H_{34}$ are fed from the video processor 62, are delayed for a predetermined time by the delaying circuits 212 and 213 and are then input into the drivers 215, 216, 217 and 218. The delayed time of the delaying circuits 212 and 213 is to compensate the displacement of the phase of the signal by the difference of the length of the insertion part of the endoscope for each type of endoscope. The clock pulses $\phi H_{12}$ and $\phi H_{34}$ are fed through the coaxial cables 204 and 205.

The resetting pulses are fed to the endoscope operating part 208 through the coaxial cable 52a and are input into the resetting terminal $\phi R$ of the solid state imaging device 16 through the coaxial cable 52b through the delaying circuit 211 and driver 214.

Thereby, the electronic parts of the endoscope tip forming part can be minimized, the phase of the driving pulses can be compensated and an observed image of a better picture quality can be obtained.

This invention is not limited to the above described embodiments. The entire cable bundle may be coated with shielding wires instead of providing the shielding wire on each cable.

Figure 30:
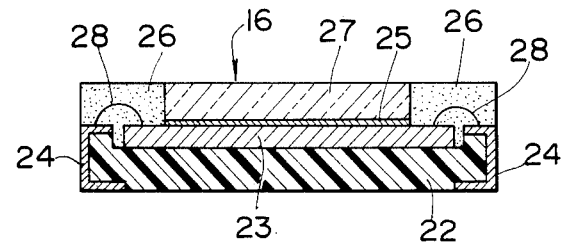
FIG. 30 is a sectioned view showing a solid state imaging device in the fifteenth embodiment.

In the solid state imaging device 16, as in the fifteenth embodiment shown in FIG. 30, the color filter array 25 may be formed directly on the cover glass 27 and may be cemented to the chip 23. In such a case, the resin 26 need not be transparent but may be a non-transparent resin.

Here, the base 22 may not be a ceramic substate but may be made of a resin. The color filter may be formed by printing on the chip 23. In such a case, the cover glass 27 may be a mere light transmitting plane plate. The cover glass may be replaced with an infrared ray cut-off filter, low pass filter or color compensating filter. Thus, according to this embodiment, the thickness direction dimension of the solid state imaging device 16 can be minimized.

Figure 31:
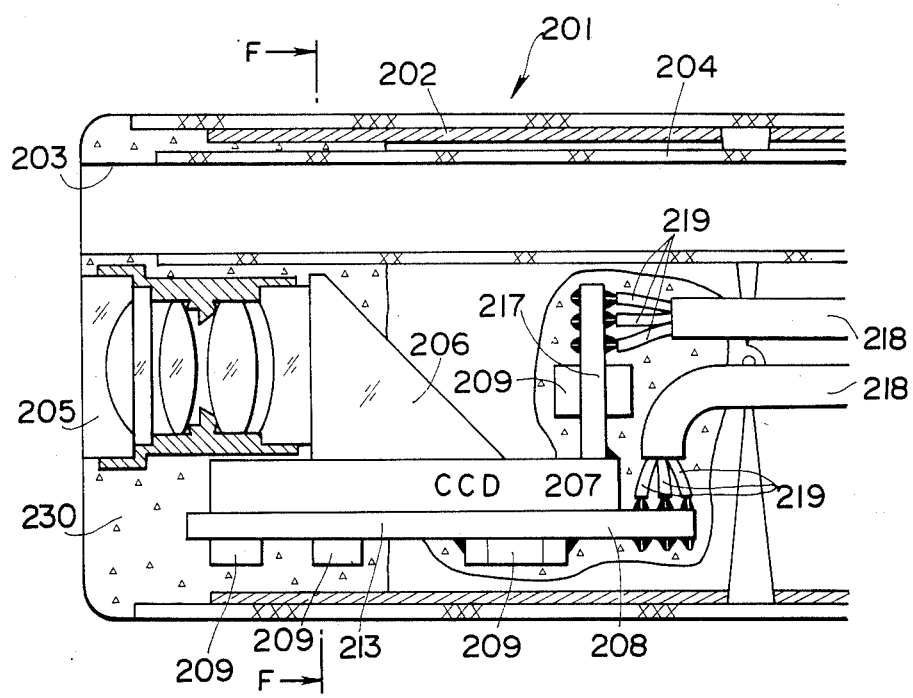

FIGS. 31 to 36 show the sixteenth embodiment of the present invention. As shown in FIG. 31, inside a tip frame 202 forming a tip part 201, in a position near the upper part, a forceps channel 203 is formed inside a channel tube 204 and an objective system 205 is arranged below the forceps channel 203. A light path changing prism 206 is arranged in a rear position (with respect to the incident light) on the optical axis of this objective system 205. A CCD (charge coupled device) 207 is so arranged that the light path may be changed to a downward light path by this prism 206 and the imaging surface may be located in the focal plane by the above mentioned objective system 205.

A substrate 208 is arranged under the above mentioned CCD 207. Electronic parts 209 such as capacitors are provided to project on the lower surface of this substrate 208.

Figure 32:
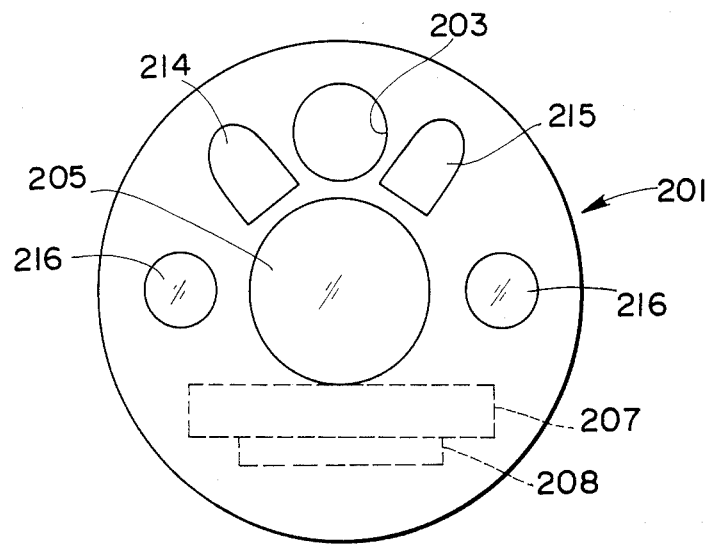
Figure 33:
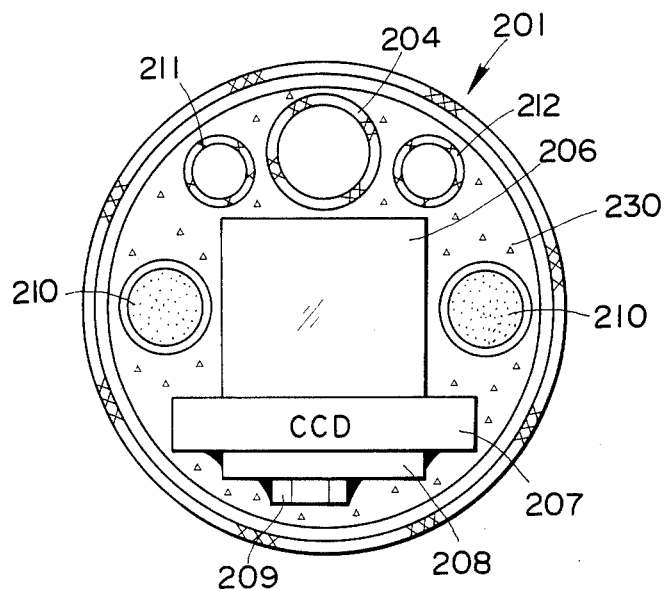

As shown in FIG. 33, light guides 210 are arranged on both sides in the horizontal direction of the above mentioned prism 206. A water feeding tube 211 and air feeding tube 212 are arranged on both sides of the forceps channel 203. As shown in FIG. 32, a water feeding nozzle 214 and air feeding nozzle 215 are formed respectively at the tips of these water feeding tube 211 and air feeding tube 212 and are directed toward the outer surface of the objective system 204. Light distributing lenses 216 are fitted to the end surfaces of the respective light guides 210 so as to be able to illuminate the object side to be imaged by the objective system 205.

As shown in FIG. 31, a substrate 217 is erected at the rear end of the upper surface of the CCD chip 207 and is fitted also with the electronic part 209.

Signal wires 219 coated with coating tubes 218 are soldered at the ends to the rear end of the substrate 208 and the upper end of the substrate 217 and are connected at the other ends to a video processor not illustrated.

Figure 34:
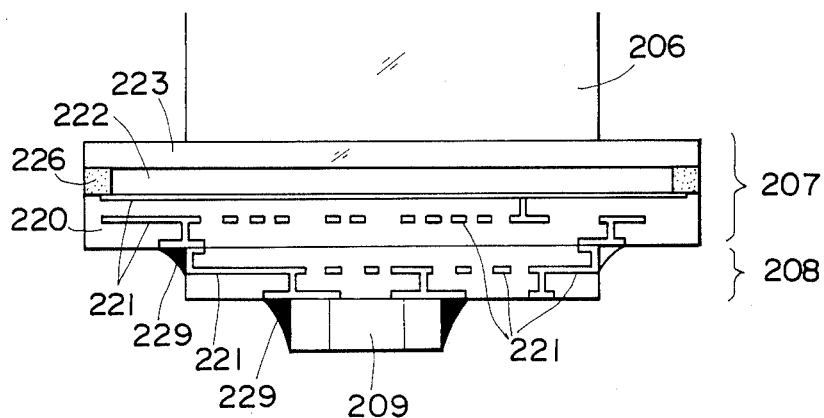
Figure 35:
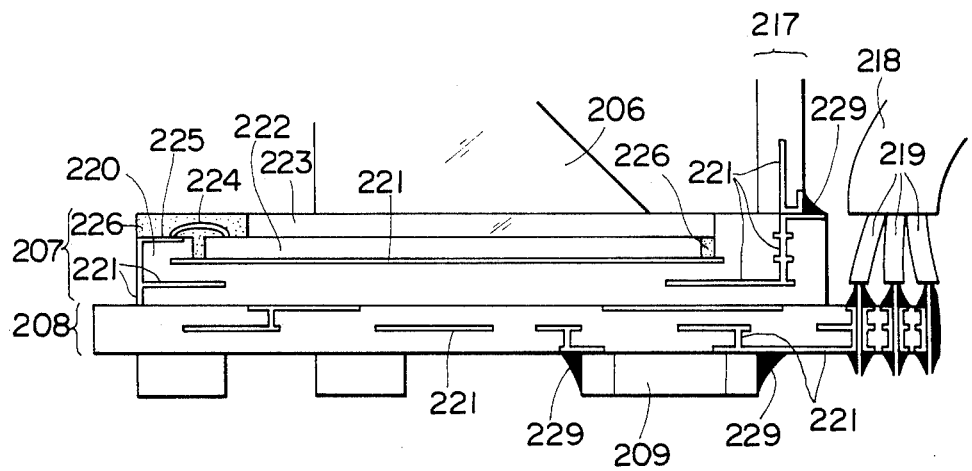

In the above mentioned CCD 207, as shown in FIGS. 34 and 35, a CCD chip 222 is fitted on the upper surface of a base member 220 through a wiring 221. A cover glass 223 is secured on the imaging surface of this CCD chip 222. A prism 206 is secured on the upper surface of this cover glass 223.

The bonding pad of the above mentioned CCD chip 222 is connected with a bonding pad 225 on the base member 220 side through a bonding wire 224 and is then sealed with a non-transparent resin 226.

The above mentioned base member 220 and substrate 208 are multilayered ceramic substrates and are wired 221 in such required positions as on the outer surfaces, inner layer surfaces and sides and between the layers.

The above mentioned base member 220 is not a flat plate but steppedly projects in the bonding pad 225 part at the front end and the substrate 217 fitting part at the rear end.

Figures 36A, 36C, 36D:
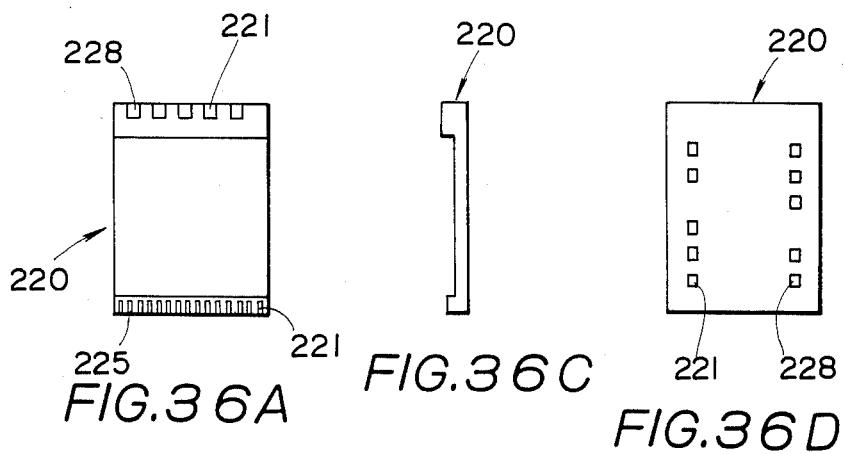
FIGS. 36A–36D shows views as seen respectively from above, forward, sideward and below a base member to which a solid state imaging device chip is attached.
Figure 36B:

By multilayering the above mentioned base member 220 and substrate 208, the substrate can be made smaller than when it is not multilayered and, as shown in FIG. 36, external electrodes can be dispersed.

Now, as shown in FIG. 36A, there are 15 bonding pads 225 on the above mentioned base member 220. If the external electrodes 228 are formed at the same pitch as these pads, when the CCD 207 and substrate 208 are soldered with each other, solder bridges will be produced. As only wire bonding may be made, the pitch of the bonding pads 225 can be made so small as to be about 0.2 mm. but the pitch of the external electrodes 228 must be more than 0.6 mm. for soldering. In this embodiment, by using the wiring 221 from the bonding pad 225 part and due to the multilayered ceramic substrate, as shown in FIG. 36A, the external electrodes 228 can be made larger in pitch than the bonding pads 225 and can be arranged as dispersed.

Now, as shown in FIG. 35, the above mentioned bonding pads 225 are provided on the scope tip side because, if the parts required to be wire-bonded, that is, the chip side bonding pads and the base side bonding pads 225 are in the lateral direction intersecting at right angles with the axis of the scope, the scope will become thicker. Also, if the bonding pads 225 are on the rear end side of the scope, the rigid tip part will be longer. Therefore, the bonding pads 225 are provided only on the tip side.

On the other hand, as shown in FIG. 36D, the external electrodes 228 on the lower surface of the CCD 207 are provided as aranged in the lengthwise direction of the scope. The width in the lateral direction of the scope of the substrate 208 is made smaller than the width in the same direction of the CCD 207 (See FIG. 34). The substrate 208 and CCD 207 are connected with each other by soldering 229. Also, as shown in FIG. 34, the CCD 207 and substrate 208 are lowered to the lowest position possible in the space within the tip frame 202 so as to make the outside diameter of the scope small. That is to say, the external electrodes 228 need not always be on the side in the same direction as of the side on which the conductive parts of the substrate are formed of the CCD 207 but may be merely in the positions corresponding to the conductive parts of the substrate 208 on the lower surface side of the CCD 207.

The CCD 207 is provided on both lower surface and upper surface with the external electrodes 228 so that the two substrates 208 and 217 may be connected with each other. Thus, the space within the tip part 201 can be more effectively utilized to make the endoscpoe compact and small.

The tip part 201 is filled within with the tip forming member 230 around the CCD 207 and the like.

Figure 37:
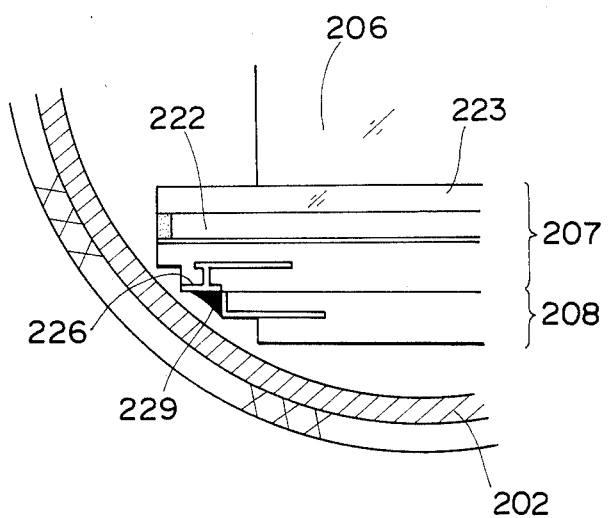
FIG. 37 is a sectioned view showing a part of a tip part of the seventeenth embodiment of the present invention.

FIG. 37 shows the important part of the seventeenth embodiment of the present invention.

This embodiment relates to the multilayered ceramic substrate part forming the CCD 207 and substrate 208 in the above mentioned sixteenth embodiment.

That is to say, the respective sheets forming the multilayered ceramic substrate are made different in the width (in the lateral direction of the scope) so that the nearer to the outside than to the center of the scope, the narrower the sheets may be, thereby the horizontal positions of the CCD's 207 and 208 may be lowered as much as possible as shown in FIG. 37 and the tip part of the scope may be smaller in diameter.

The width of the lower surface of the CCD 207 is smaller than the width of the CCD chip 222. In the above described embodiment, the size of the base member 220 is larger than that of the CCD chip 222 but, in this embodiment, a part of the lower surface not in contact with the base member 220 of the chip 222 is made smaller than the base member 220.

The above described respective embodiments can be combined to form a different embodiment.

According to this invention, in an endoscope having a solid state imaging device in the tip part, the imaging part can be made smaller and the containing efficiency of the tip part can be elevated. Further, by making the insertion part smaller in diameter, the pain to the patient can be reduced and the utilization to finer parts becomes possible.

What is claimed is:
1. An endoscope having:
an image forming objective system contained in the tip part of an insertion part formed to be elongate so as to be insertable into a body cavity or the like;
a solid state imaging device having a photoelectric converting function and arranged so as to have its imaging surface located in the focal plane of said objective system; and
a substrate having said solid state imaging device fixed thereon and having conductive parts electrically connected with the electrodes of said solid state imaging device,
characterized in that said conductive parts are formed on at least one side surface of said substrate and said solid state imaging device is fitted onto said substrate while, for electrodes located on at least one end surface side in said solid state imaging device placed on said substrate so as to be adjacent to said conductive parts, one side surface of said conductive parts retreats to be below the same level as of said electrode position.

2. An endoscope according to claim 1 wherein the plate surface of said solid state imaging device is arranged substantially parallel with the long axis direction of the endoscope, the wire bonding part of said solid state imaging device is formed on an end side intersecting substantially at right angles with the long axis direction of the endoscope and at least a part of the electrodes of the solid state imaging device are formed substantially along the long axis direction of the endoscope.

3. An endoscope according to claim 1 or 2 wherein the electrodes of said solid state imaging device are provided on the lower surface of the base of said solid state imaging device and the electrodes on the lower surface of the base of said solid state imaging device and the conductive parts of said substrate are electrically connected with each other.

4. An endoscope according to claim 1 or 2 wherein the width of the conductive part forming direction in the substrate of said solid state imaging device is larger than the width of the conductive part forming direction of said substrate.

5. An endoscope according to claim 1 or 2 wherein electronic parts are fitted on the substrate in the part arranged as projected from the side of said solid state imaging device.

6. An endoscope according to claim 5 wherein the imaging surface of said solid state imaging device is positioned in a plane including the diameter substantially passing through the center axis of the endoscope.

7. An endoscope according to claim 6 wherein the conductive parts formed on at least one side surface of said substrate are plural and an insulating part for preventing short-circuiting is formed to project between the adjacent conductive parts.

8. An endoscope according to claim 6 wherein the center position of said imaging surface is arranged to be eccentric to one side from said center axis and a light guide forming an illuminating means is arranged on the other side.

9. An endoscope according to claim 1 wherein said substrate is formed of a multilayered ceramic substrate.

10. An endoscope according to claim 1 wherein said solid state imaging device is formed of a multilayered ceramic substrate.

11. An endoscope according to claim 1 wherein said substrate is formed of a multilayered ceramic substrate and said solid state imaging device is formed of a multilayered ceramic substrate.

12. An endoscope according to claim 10 wherein the pitch between the adjacent electrodes connected at the other ends with the bonding pads of a solid state imaging device chip by using said multilayered ceramic substrate and connected with the substrate side is made larger than the pitch of the bonding pads of said solid state imaging device chip.

13. An endoscope according to claim 10 wherein the electrodes to be connected with the substrate side are arranged as dispersed by using said multilayered ceramic substrate.

14. An endoscope according to claim 9 or 10 wherein said multilayered ceramic substrate is made a step shorter in the substrate part on the side near the outer periphery of the tip part.

15. An endoscope according to claim 1 wherein said solid state imaging device has the parts to which a solid state imaging device chip is die-bonded and the electrode parts formed of the same metal plates.

16. An endoscope according to claim 1 wherein the electrodes of said solid state imaging device are provided on the lower surface of the base of said solid state imaging device and the electrodes on the lower surface of the base of said solid state imaging device and the conductive parts of said substrate are electrically connected with each other and wherein the width of the conductive part forming direction in the substrate of said solid state imaging device is larger than the width of the conductive part forming direction of said substrate.

17. An endoscope according to claim 2 where the electrodes of said solid state imaging device are provided on the lower surface of the base of said solid state imaging device and the electrodes on the lower surface of the base of said solid state imaging device and the conductive parts of said substrate are electrically connected with each other and wherein the width of the conductive part forming direction in the substrate of said solid state imaging device is larger than the width of the conductive part forming direction of said substrate.

18. An endoscope according to claim 16 wherein electronic parts are fitted on the substrate in the part arranged as projected from the side of said solid state imaging device.

19. An endoscope according to claim 17 wherein electronic parts are fitted on the substrate in the part arranged as projected from the side of said solid state imaging device.

20. An endoscope according to claims 16, 17, 18, or 19 wherein the imaging surface of the solid state imaging device is positioned in a plane including the diameter substantially passing through the center axis of the endoscope and wherein the conductive parts formed on at least one side surface of said substrate are plural and an insulating part for preventing shortcircuiting is formed to project between the adjacent conductive parts.

21. An endoscope having:
   an image forming objective system contained in the tip part of an insertion part formed to be elongate so as to be insertable into a body cavity or the like;
   a solid state imaging device having a photoelectric converting function and arranged so as to have its imaging surface located in the focal plane of said objective system; and
   a substrate having said solid state imaging device fixed thereon and having conductive parts electrically connected with the electrodes of said solid state imaging device,
   wherein said solid state imaging device comprises:
   a base member having conductive parts;
   a solid state imaging device chip die-bonded on said base member;
   a transparent plate pasted to cover the imaging surface of said solid state imaging device chip;
   bonding wires connecting both bonding pads of said solid state imaging device chip and said base member; and
   a non-transparent resin sealing the connecting parts through said bonding wires in the side parts of said transparent plate.

22. An endoscope according to claim 21 wherein a color filter array is interposed between said solid state imaging device chip and said transparent plate.

* * * * *